US00PP24971P3

(12) United States Plant Patent
Meilland

(10) Patent No.: US PP24,971 P3
(45) Date of Patent: Oct. 21, 2014

(54) GRANDIFLORA ROSE PLANT NAMED 'MEIZAMBAIZT'

(50) Latin Name: *Rosa hybrida*
Varietal Denomination: Meizambaizt

(71) Applicant: CP Delaware, Inc., Wilmington, DE (US)

(72) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 92 days.

(21) Appl. No.: 13/815,319

(22) Filed: Feb. 21, 2013

(65) Prior Publication Data

US 2014/0215658 P1 Jul. 31, 2014

(30) Foreign Application Priority Data

Jan. 28, 2013 (QZ) ..... PBR 20130325

(51) Int. Cl.
*A01H 5/00* (2006.01)

(52) U.S. Cl.
USPC ..... Plt./134

(58) Field of Classification Search
USPC ..... Plt./134
See application file for complete search history.

*Primary Examiner* — Annette Para

(74) *Attorney, Agent, or Firm* — Buchanan, Ingersoll & Rooney PC

(57) ABSTRACT

A new and distinct variety of Grandiflora rose plant is provided that abundantly and substantially continuously forms attractive double cup-shaped yellow blossoms. The vegetation is very strong. A bushy growth habit is displayed. The foliage is dense dark green with a glossy upper surface. The tolerance to disease is very good, particularly with respect to black spot. The plant is well suited for providing distinctive attractive ornamentation in the landscape.

1 Drawing Sheet

Botanical/commercial classification: *Rosa hybrida*/Grandiflora Rose Plant.

Varietal denomination: cv. Meizambaizt.

SUMMARY OF THE INVENTION

The new variety of *Rosa hybrida* Grandiflora rose plant was created in France by artificial pollination wherein two parents were crossed which previously had been studied in the hope that they would contribute the desired characteristics. The female parent (i.e., the seed parent) was the product of the cross of the 'Macivy' variety (U.S. Plant Pat. No. 8,362) and an unnamed and unreleased seedling (non-patented in the United States). The male parent (i.e., pollen parent) was the 'Wekamanda' variety (U.S. Plant Pat. No. 9,591).

The parentage of the new variety can be summarized as follows:

('Macivy'×Unnamed Seedling)×'Wekamanda'.

The seeds resulting from the above pollination were sown and small plants were obtained which were physically and biologically different from each other. Selective study resulted in the identification of a single plant of the new variety.

It was found that the new Grandiflora rose plant of the present invention:

(a) forms very strong vegetation,
(b) exhibits a bushy growth habit with very dense dark green foliage having a glossy upper surface,
(c) abundantly and substantially continuously forms attractive double cup-shaped yellow blossoms,
(d) displays a very good tolerance to disease, and
(e) is well suited for providing distinctive attractive ornamentation in the landscape.

The yellow blossom coloration blends nicely with the dense glossy dark green foliage. The tolerance to disease is particularly good with respect to black spot. The ability to bloom is considered to be exceptional.

The new variety well meets the needs of the horticultural industry and can be grown to advantage as colorful ornamentation in parks and gardens.

The new variety can be readily distinguished from its ancestors upon an inspection of the blossoms. More specifically, the 'Macivy' ancestor is a Floribunda rose that forms red blossoms with some yellow near the base. The 'Wekamanda' male parent variety is a Hybrid Tea rose that forms light yellow blossoms with a greenish hue on the outer petals when newly opened.

The new variety has been found to undergo asexual propagation at Le Cannet des Maures, Var, France, by a number of routes, including budding, grafting, and the use of cuttings. Such asexual propagation by the above-mentioned techniques has shown that the characteristics of the new variety are stable and are strictly transmissible by such asexual propagation from one generation to another. Accordingly, the new variety undergoes asexual propagation in a true-to-type manner.

The new variety has been named 'Meizambaizt'.

BRIEF DESCRIPTION OF THE PHOTOGRAPH

The accompanying photograph shows as nearly true as it is reasonably possible to make the same in a color illustration of this character, typical specimens of plant parts of the new variety. The rose plants of the new variety were approximately two years of age and were observed during October while budded on *Rosa laxa* rootstock and growing outdoors at Le Cannet des Maures, Var, France. Standard color information is provided at the bottom of the photograph for comparative purposes.

DETAILED DESCRIPTION

Figures 1, 2, 3, 4, 5, 6, 7, 8, 9, 10, 11, 12, 13, 14, 15:
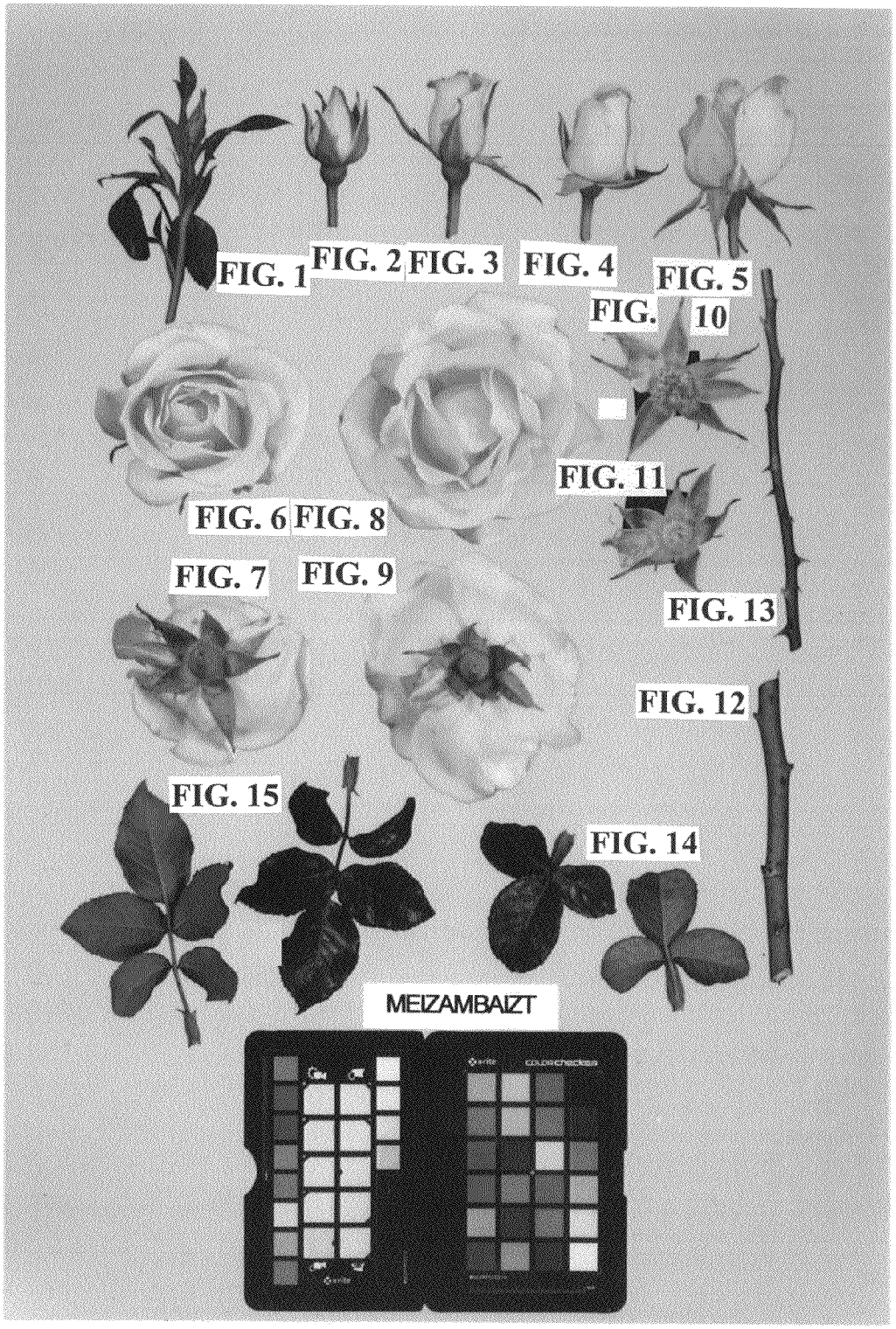
FIG. 1 illustrates a specimen of a young shoot.
FIG. 2 illustrates a specimen of a floral bud at the opening of the sepals.
FIG. 3 illustrates a specimen of a floral bud at the further opening of the sepals and the initiation of petal opening.
FIG. 4 illustrates a specimen of a floral bud at the further opening of the petals.
FIG. 5 illustrates a specimen of a flower in the course of opening.
FIG. 6 illustrates a specimen of an open flower — plan view — obverse.
FIG. 7 illustrates a specimen of an open flower — plan view — reverse.
FIG. 8 illustrates a specimen of a fully open flower — plan view — obverse.
FIG. 9 illustrates a specimen of a fully open flower — plan view — reverse.
FIG. 10 illustrates a specimen of a floral receptacle showing arrangement of the stamens and pistils.
FIG. 11 illustrates a specimen of a floral receptacle showing arrangement of the pistils (stamens removed)
FIG. 12 illustrates a specimen of a main branch.
FIG. 13 illustrates a specimen of a flowering stem.
FIG. 14 illustrates specimens of leaves with 3 leaflets — plan view — upper surface (left) and — under surface (right)
FIG. 15 illustrates specimens of leaves with 5 leaflets — plan view — upper surface (right) and — under surface (left).

The chart used in the identification of the colors is that of The Royal Horticultural Society (R.H.S. Colour Chart—1995 or equivalent) except where ordinary color terms are utilized. Common color terms are to be accorded their customary dictionary significance. The description is based upon the observation of plants of the new variety at an age of approximately two years during the month of May while being grown outdoors while budded on *Rosa laxa* rootstock at Le Cannet des Maures, Var, France.

Class: Grandiflora.

Plant:

*Growth habit.*—Bushy.

Branches:

*Color.*—Young stems: commonly near Yellow-Green Group 146B and 146C. Adult wood: commonly near Yellow-Green Group 147B.

*Thorns.*—Configuration: curved downwards and slightly concave on the under surface with an oval base. On young stems: commonly absent. Quantity and size on adult stems: commonly approximately 8 on average having lengths of approximately 1.1 cm over a stem length of 10 cm. Color on adult stems: near Greyed-Orange Group 167C.

Leaves:

*Overall appearance.*—Dense dark green.

*Leaflets.*—Shape: generally oval. Number: 3, and most often 5 and 7.

*Size.*—Terminal leaflets commonly are approximately 6.4 cm in length on average and approximately 4 cm in width on average. Apex: generally cuspidate. Base: rounded. Serration: slightly denticulate, small and single. Texture: firm, and leathery, and glossy on the upper surface. Color (young foliage): near Green Group 137B on the upper surface, and near Yellow-Green Group 146B on the under surface. Color (adult foliage): near Green Group 139A on the upper surface, and near Green Group 137B on the under surface.

*Petiole.*—Length: commonly approximately 3.8 cm on average. Texture: slightly glandular on the upper surface and commonly with a few prickles on the under surface. Color: near Green Group 137B on the upper surface, and near Green Group 137C on the under surface.

*Rachis.*—Color: near Green Group 137C on the upper surface, and near Yellow-Green Group 137C on the under surface.

*Stipules.*—General appearance: adnate, pectinate, and rather broad. Size: commonly approximately 2.1 cm in length on average, and approximately 6 mm in width on average. Color: near Green Group 137B on the upper surface, and near Green Group 137C on the under surface.

Inflorescence:

*Number of flowers.*—Commonly approximately 2 to 5 blossoms per stem.

*Buds.*—Shape: generally conical and medium in size. Length: approximately 2.7 cm on average. Width: approximately 1.9 cm at the widest point on average. Color: as the calyx breaks: on the upper surface near Yellow Group 13B and margined with Orange-Red Group 30C and 30D, and on the under surface near Yellow Group 13B margined with near Orange-Red Group 30C and 30D.

*Flower.*—Diameter: approximately 10 to 11 cm on average when fully open. Shape: cup-shaped. Color (in course of opening): Upper side: near Yellow Group 13B margined with near Orange-Red Group 30D. Under side: near Yellow-Orange Group 15C margined with near Orange-Red Group 30B. Color (when open): Upper side: near Yellow Group 12C and more or less margined and suffused with Orange Group 28D. Under side: near Yellow Group 12C and very slightly suffused with near Orange Group 28D. Fragrance: none. Petal number: commonly approximately 22 to 26 on average under normal growing conditions. Petal shape: commonly display a rounded tip and an obtuse base. Petal arrangement: imbricated and commonly without petaloids. Petal texture: firm and leathery. Petal length: commonly approximately 5.5 cm on average. Petal width: commonly approximately 4 cm on average. Petal drop: good with the petals commonly detaching cleanly before drying. Stamen number: commonly approximately 108 on average. Anthers: arranged regularly around the styles, commonly approximately 2 mm in size on average, and near Yellow Group 13C in coloration. Filaments: commonly approximately 1.1 to 1.5 cm in length on average, and near Yellow Group 13A in coloration. Pistils: commonly approximately 76 on average. Styles: commonly approximately 6 mm in size on average, and near Yellow Group 4D in coloration. Stigmas: commonly approximately 2 mm in size and near Orange-Red Group 34B in coloration.

*Receptacle.*—Length: commonly approximately 9 mm on average. Width: commonly approximately 12 mm on average at widest point. Shape: funnel-shaped. Texture: smooth. Color: near Yellow-Green Group 146D.

*Sepals.*—Length: commonly approximately 3.2 cm on average. Width: commonly approximately 1 cm on average at the widest point. Shape: longish and narrow and commonly upright upon initial opening. Texture: tomentose on the upper surface and smooth on the under surface. Color: commonly near Yellow-Green Group 147D on the upper surface and near Yellow-Green Group 146D on the under surface.

*Peduncle.*—Length: commonly approximately 6 cm on average. Width: commonly approximately 7 mm on average. Texture: smooth. Color: near Yellow-Green Group 146D.

Development:

*Vegetation.*—Very strong.

*Blooming.*—Early season, very abundant and substantially continuous.

*Tolerance to diseases.*—Very good, particularly with respect to black spot.

I claim:

1. A new and distinct Grandiflora rose plant characterized by the following characteristics:

(a) forms very strong vegetation, (b) exhibits a bushy growth habit with very dense dark green foliage having a glossy upper surface, (c) abundantly and substantially continuously forms attractive double cup-shaped yellow blossoms, (d) displays very good tolerance to disease, and (e) is well suited for providing distinctive attractive ornamentation in the landscape;

substantially as shown and described.

* * * * *

MEIZAMBAIZT